(12) United States Patent
Koka et al.

(10) Patent No.: US 11,918,411 B2
(45) Date of Patent: Mar. 5, 2024

(54) INTRAOPERATIVE DETECTION OF ELECTRODE LEAD MISPLACEMENT DURING A LEAD INSERTION PROCEDURE

(71) Applicant: Advanced Bionics AG, Staefa (CH)

(72) Inventors: Kanthaiah Koka, Valencia, CA (US); Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 99 days.

(21) Appl. No.: 17/089,535

(22) Filed: Nov. 4, 2020

(65) Prior Publication Data
US 2021/0128104 A1  May 6, 2021

Related U.S. Application Data

(60) Provisional application No. 62/931,706, filed on Nov. 6, 2019.

(51) Int. Cl.
*A61B 8/08* (2006.01)
*A61B 5/00* (2006.01)
*A61B 5/24* (2021.01)

(52) U.S. Cl.
CPC ............. *A61B 8/0841* (2013.01); *A61B 5/24* (2021.01); *A61B 5/743* (2013.01)

(58) Field of Classification Search
CPC ......... A61B 8/0841; A61B 5/24; A61B 5/743; A61B 5/388; A61B 5/125; A61B 5/38; A61N 1/36039; A61N 1/36038; A61N 1/0541; H04R 25/30; H04R 2225/67
See application file for complete search history.

(56) References Cited

U.S. PATENT DOCUMENTS

| | | | | |
|---|---|---|---|---|
| 11,273,283 B2 * | 3/2022 | Poltorak | ............... | A61M 21/02 |
| 2016/0243361 A1 * | 8/2016 | Litvak | ................ | A61N 1/36039 |
| 2017/0232257 A1 * | 8/2017 | Koka | ................... | A61N 1/0541 |
| | | | | 607/3 |
| 2018/0056058 A1 * | 3/2018 | Heasman | ............... | A61B 5/686 |
| 2018/0110982 A1 * | 4/2018 | Heasman | ............. | H04R 25/356 |
| 2018/0229035 A1 * | 8/2018 | Koka | ................ | A61N 1/36039 |
| 2018/0288536 A1 * | 10/2018 | Karunasiri | ........... | H04R 25/554 |
| 2018/0304069 A1 * | 10/2018 | Koka | ................. | A61N 1/36039 |
| 2019/0030323 A1 * | 1/2019 | Koka | ................... | A61N 1/0541 |

FOREIGN PATENT DOCUMENTS

WO   WO-2017131675 A1 *  8/2017  ........... A61N 1/0541

\* cited by examiner

*Primary Examiner* — Boniface N Nganga
*Assistant Examiner* — Zainab Mohammed Aldarraji
(74) *Attorney, Agent, or Firm* — ALG Intellectual Property, LLC

(57) ABSTRACT

An exemplary diagnostic system may be configured to direct an acoustic stimulation generator to apply acoustic stimulation to a recipient of a cochlear implant during an insertion procedure in which an electrode lead coupled to the cochlear implant is supposed to be inserted into a cochlea of the recipient, direct the cochlear implant to use an electrode on the electrode lead to record an evoked response signal that occurs within the recipient in response to the acoustic stimulation, detect an anomaly in the evoked response signal, and determine, based on the anomaly, that the electrode lead is being inserted into a vestibular canal instead of into the cochlea.

19 Claims, 9 Drawing Sheets

INTRAOPERATIVE DETECTION OF ELECTRODE LEAD MISPLACEMENT DURING A LEAD INSERTION PROCEDURE

RELATED APPLICATIONS

The present application claims priority under 35 U.S.C. § 119(e) to U.S. Provisional Patent Application No. 62/931,706, filed Nov. 6, 2019, the contents of which are hereby incorporated by reference in their entirety.

BACKGROUND INFORMATION

During a lead insertion procedure, a practitioner (e.g., a surgeon) may attempt to insert an electrode lead into a cochlea of a recipient. Due to inner ear malformations and/or other factors, the electrode lead may inadvertently enter a vestibular canal instead of the cochlea. Heretofore, misplacement of an electrode lead within the vestibular canal may not be readily detected intraoperatively. This is because the surgeon cannot see where the electrode lead is being placed and because conventional intraoperative measurements, such as impedance measurements and electrically evoked compound action potential (eCAP) measurements, are not indicative of such misplacement.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for intraoperative detection of electrode lead misplacement during a lead insertion procedure are described herein. For example, a diagnostic system may be configured to direct an acoustic stimulation generator to apply acoustic stimulation to a recipient of a cochlear implant during an insertion procedure in which an electrode lead coupled to the cochlear implant is supposed to be inserted into a cochlea of the recipient, direct the cochlear implant to use an electrode on the electrode lead to record an evoked response signal that occurs within the recipient in response to the acoustic stimulation, detect an anomaly in the evoked response signal, and determine, based on the anomaly, that the electrode lead is being inserted into a vestibular canal instead of into the cochlea. Based on this determination, the diagnostic system may perform one or more remedial actions, such as providing a notification, stopping the insertion procedure, and/or retracting the electrode lead.

As used herein, an evoked response signal may be representative of one or more evoked responses that occur within a recipient in response to acoustic stimulation being applied to the recipient. The evoked responses may each be an electrocochleographic (ECochG) potential or response (e.g., a cochlear microphonic (CM) response and/or a auditory nerve neurophonics (ANN) response), an auditory nerve response, a brainstem response, a compound action potential, a stapedius reflex, and/or any other type of neural or physiological response that may occur within a recipient in response to application of acoustic stimulation to the recipient. Evoked responses may originate from neural tissues, hair cell to neural synapses, inner or outer hair cells, and/or other sources.

The systems and methods described herein advantageously facilitate intraoperative detection of inadvertent placement of an electrode lead in a vestibular canal. This may allow a surgeon and/or other user to ascertain and correct such an inadvertent placement in substantially real time during the insertion procedure, thereby resulting in shorter and more effective insertion procedures.

Figure 1:
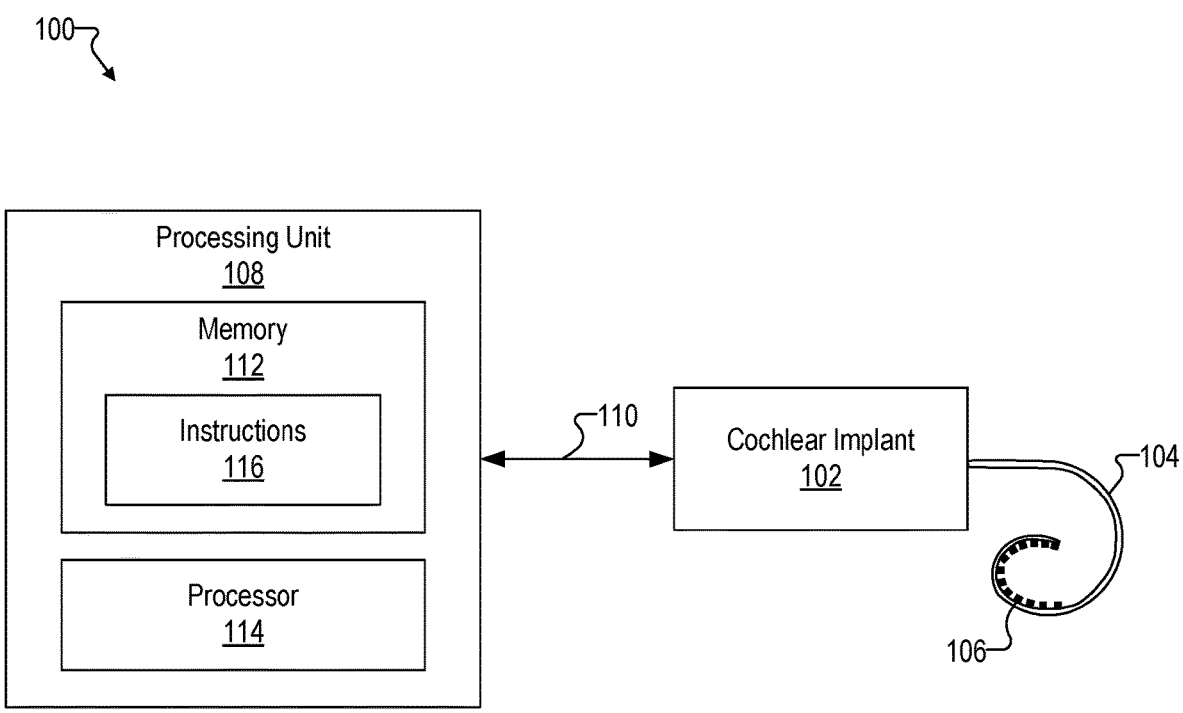
FIG. 1 illustrates an exemplary cochlear implant system.

FIG. 1 illustrates an exemplary cochlear implant system 100 configured to be used by a recipient. As shown, cochlear implant system 100 includes a cochlear implant 102, an electrode lead 104 physically coupled to cochlear implant 102 and having an array of electrodes 106, and a processing unit 108 configured to be communicatively coupled to cochlear implant 102 by way of a communication link 110.

The cochlear implant system 100 shown in FIG. 1 is unilateral (i.e., associated with only one ear of the recipient). Alternatively, a bilateral configuration of cochlear implant system 100 may include separate cochlear implants and electrode leads for each ear of the recipient. In the bilateral configuration, processing unit 108 may be implemented by a single processing unit configured to interface with both cochlear implants or by two separate processing units each configured to interface with a different one of the cochlear implants.

Cochlear implant 102 may be implemented by any suitable type of implantable stimulator configured to apply electrical stimulation to one or more stimulation sites located along an auditory pathway of the recipient. In some examples, cochlear implant 102 may additionally or alternatively apply nonelectrical stimulation (e.g., mechanical and/or optical stimulation) to the auditory pathway of the recipient.

In some examples, cochlear implant 102 may be configured to generate electrical stimulation representative of an audio signal processed by processing unit 108 in accordance with one or more stimulation parameters transmitted to cochlear implant 102 by processing unit 108. Cochlear implant 102 may be further configured to apply the electrical stimulation to one or more stimulation sites (e.g., one or more intracochlear locations) within the recipient by way of one or more electrodes 106 on electrode lead 104. In some examples, cochlear implant 102 may include a plurality of independent current sources each associated with a channel defined by one or more of electrodes 106. In this manner, different stimulation current levels may be applied to multiple stimulation sites simultaneously by way of multiple electrodes 106.

Cochlear implant 102 may additionally or alternatively be configured to generate, store, and/or transmit data. For example, cochlear implant may use one or more electrodes 106 to record one or more signals (e.g., one or more voltages, impedances, evoked responses within the recipient, and/or other measurements) and transmit, by way of communication link 110, data representative of the one or more signals to processing unit 108. In some examples, this data is referred to as back telemetry data.

Electrode lead 104 may be implemented in any suitable manner. For example, a distal portion of electrode lead 104 may be pre-curved such that electrode lead 104 conforms with the helical shape of the cochlea after being implanted. Electrode lead 104 may alternatively be naturally straight or of any other suitable configuration.

In some examples, electrode lead 104 includes a plurality of wires (e.g., within an outer sheath) that conductively couple electrodes 106 to one or more current sources within cochlear implant 102. For example, if there are n electrodes 106 on electrode lead 104 and n current sources within cochlear implant 102, there may be n separate wires within electrode lead 104 that are configured to conductively connect each electrode 106 to a different one of the n current sources. Exemplary values for n are 8, 12, 16, or any other suitable number.

Electrodes 106 are located on at least a distal portion of electrode lead 104. In this configuration, after the distal portion of electrode lead 104 is inserted into the cochlea, electrical stimulation may be applied by way of one or more of electrodes 106 to one or more intracochlear locations. One or more other electrodes (e.g., including a ground electrode, not explicitly shown) may also be disposed on other parts of electrode lead 104 (e.g., on a proximal portion of electrode lead 104) to, for example, provide a current return path for stimulation current applied by electrodes 106 and to remain external to the cochlea after the distal portion of electrode lead 104 is inserted into the cochlea. Additionally or alternatively, a housing of cochlear implant 102 may serve as a ground electrode for stimulation current applied by electrodes 106.

Processing unit 108 may be configured to interface with (e.g., control and/or receive data from) cochlear implant 102. For example, processing unit 108 may transmit commands (e.g., stimulation parameters and/or other types of operating parameters in the form of data words included in a forward telemetry sequence) to cochlear implant 102 by way of communication link 110. Processing unit 108 may additionally or alternatively provide operating power to cochlear implant 102 by transmitting one or more power signals to cochlear implant 102 by way of communication link 110. Processing unit 108 may additionally or alternatively receive data from cochlear implant 102 by way of communication link 110. Communication link 110 may be implemented by any suitable number of wired and/or wireless bidirectional and/or unidirectional links.

As shown, processing unit 108 includes a memory 112 and a processor 114 configured to be selectively and communicatively coupled to one another. In some examples, memory 112 and processor 114 may be distributed between multiple devices and/or multiple locations as may serve a particular implementation.

Memory 112 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory (RAM), and an optical disc. Exemplary volatile storage media include, but are not limited to, RAM (e.g., dynamic RAM).

Memory 112 may maintain (e.g., store) executable data used by processor 114 to perform one or more of the operations described herein. For example, memory 112 may store instructions 116 that may be executed by processor 114 to perform any of the operations described herein. Instructions 116 may be implemented by any suitable application, program (e.g., sound processing program), software, code, and/or other executable data instance. Memory 112 may also maintain any data received, generated, managed, used, and/or transmitted by processor 114.

Processor 114 may be configured to perform (e.g., execute instructions 116 stored in memory 112 to perform) various operations with respect to cochlear implant 102.

To illustrate, processor 114 may be configured to control an operation of cochlear implant 102. For example, processor 114 may receive an audio signal (e.g., by way of a microphone communicatively coupled to processing unit 108, a wireless interface (e.g., a Bluetooth interface), and/or a wired interface (e.g., an auxiliary input port)). Processor 114 may process the audio signal in accordance with a sound processing program (e.g., a sound processing program stored in memory 112) to generate appropriate stimulation parameters. Processor 114 may then transmit the stimulation parameters to cochlear implant 102 to direct cochlear implant 102 to apply electrical stimulation representative of the audio signal to the recipient.

In some implementations, processor 114 may also be configured to apply acoustic stimulation to the recipient. For example, a receiver (also referred to as a loudspeaker) may be optionally coupled to processing unit 108. In this configuration, processor 114 may deliver acoustic stimulation to the recipient by way of the receiver. The acoustic stimulation may be representative of an audio signal (e.g., an amplified version of the audio signal), configured to elicit an evoked response within the recipient, and/or otherwise configured. In configurations in which processor 114 is configured to both deliver acoustic stimulation to the recipient and direct cochlear implant 102 to apply electrical stimulation to the recipient, cochlear implant system 100 may be referred to as a bimodal hearing system and/or any other suitable term.

Processor 114 may be additionally or alternatively configured to receive and process data generated by cochlear implant 102. For example, processor 114 may receive data representative of a signal recorded by cochlear implant 102 using one or more electrodes 106 and, based on the data, adjust one or more operating parameters of processing unit 108. Additionally or alternatively, processor 114 may use the data to perform one or more diagnostic operations with respect to cochlear implant 102 and/or the recipient.

Other operations may be performed by processor 114 as may serve a particular implementation. In the description provided herein, any references to operations performed by processing unit 108 and/or any implementation thereof may be understood to be performed by processor 114 based on instructions 116 stored in memory 112.

Figure 2:
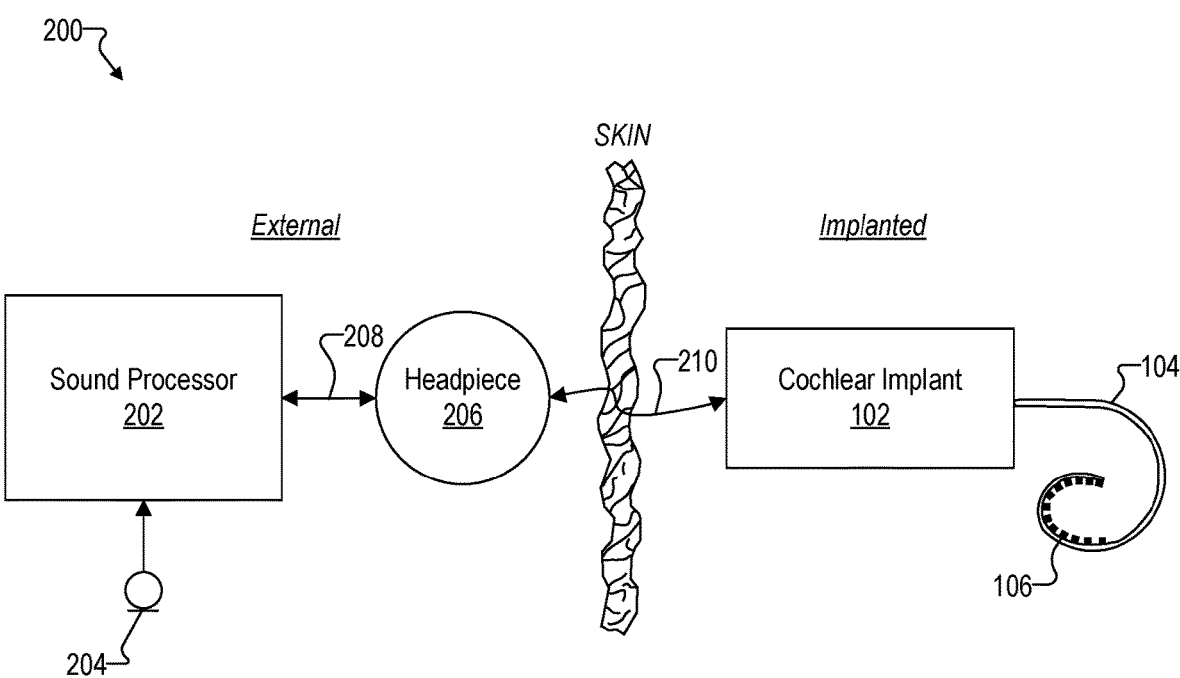
FIG. 2 shows an exemplary configuration of the cochlear implant system of FIG. 1.

Processing unit 108 may be implemented by one or more devices configured to interface with cochlear implant 102. To illustrate, FIG. 2 shows an exemplary configuration 200 of cochlear implant system 100 in which processing unit 108 is implemented by a sound processor 202 configured to be located external to the recipient. In configuration 200, sound processor 202 is communicatively coupled to a microphone 204 and to a headpiece 206 that are both configured to be located external to the recipient.

Sound processor 202 may be implemented by any suitable device that may be worn or carried by the recipient. For example, sound processor 202 may be implemented by a behind-the-ear (BTE) unit configured to be worn behind and/or on top of an ear of the recipient. Additionally or alternatively, sound processor 202 may be implemented by an off-the-ear unit (also referred to as a body worn device) configured to be worn or carried by the recipient away from the ear. Additionally or alternatively, at least a portion of sound processor 202 is implemented by circuitry within headpiece 206.

Microphone 204 is configured to detect one or more audio signals (e.g., that include speech and/or any other type of sound) in an environment of the recipient. Microphone 204 may be implemented in any suitable manner. For example, microphone 204 may be implemented by a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 202. Additionally or alternatively, microphone 204 may be implemented by one or more microphones in or on headpiece 206, one or more microphones in or on a housing of sound processor 202, one or more beam-forming microphones, and/or any other suitable microphone as may serve a particular implementation.

Headpiece 206 may be selectively and communicatively coupled to sound processor 202 by way of a communication link 208 (e.g., a cable or any other suitable wired or wireless communication link), which may be implemented in any suitable manner. Headpiece 206 may include an external antenna (e.g., a coil and/or one or more wireless communication components) configured to facilitate selective wireless coupling of sound processor 202 to cochlear implant 102. Headpiece 206 may additionally or alternatively be used to selectively and wirelessly couple any other external device to cochlear implant 102. To this end, headpiece 206 may be configured to be affixed to the recipient's head and positioned such that the external antenna housed within headpiece 206 is communicatively coupled to a corresponding implantable antenna (which may also be implemented by a coil and/or one or more wireless communication components) included within or otherwise connected to cochlear implant 102. In this manner, stimulation parameters and/or power signals may be wirelessly and transcutaneously transmitted between sound processor 202 and cochlear implant 102 by way of a wireless communication link 210.

In configuration 200, sound processor 202 may receive an audio signal detected by microphone 204 by receiving a signal (e.g., an electrical signal) representative of the audio signal from microphone 204. Sound processor 202 may additionally or alternatively receive the audio signal by way of any other suitable interface as described herein. Sound processor 202 may process the audio signal in any of the ways described herein and transmit, by way of headpiece 206, stimulation parameters to cochlear implant 102 to direct cochlear implant 102 to apply electrical stimulation representative of the audio signal to the recipient.

In an alternative configuration, sound processor 202 may be implanted within the recipient instead of being located external to the recipient. In this alternative configuration, which may be referred to as a fully implantable configuration of cochlear implant system 100, sound processor 202 and cochlear implant 102 may be combined into a single device or implemented as separate devices configured to communicate one with another by way of a wired and/or wireless communication link. In a fully implantable implementation of cochlear implant system 100, headpiece 206 may not be included and microphone 204 may be implemented by one or more microphones implanted within the recipient, located within an ear canal of the recipient, and/or external to the recipient.

Figure 3:
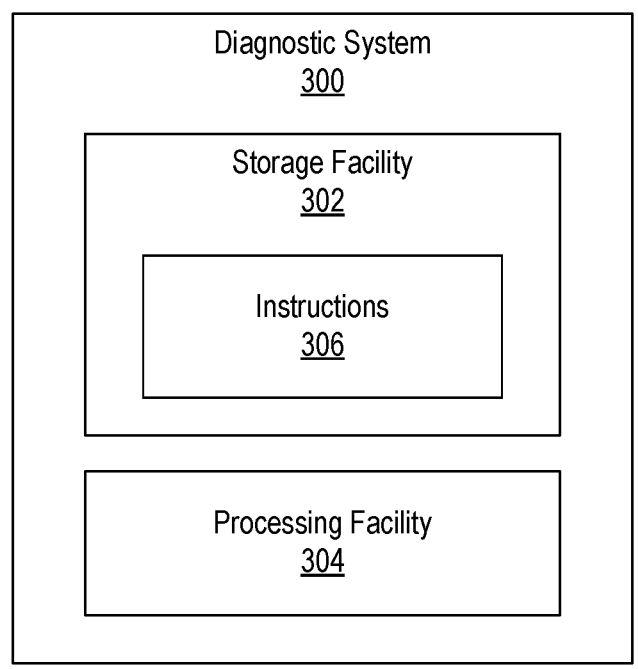
FIG. 3 illustrates an exemplary diagnostic system.

FIG. 3 illustrates an exemplary diagnostic system 300 that may be configured to perform any of the operations described herein. As shown, diagnostic system 300 may include, without limitation, a storage facility 302 and a processing facility 304 selectively and communicatively coupled to one another. Facilities 302 and 304 may each include or be implemented by hardware and/or software components (e.g., processors, memories, communication interfaces, instructions stored in memory for execution by the processors, etc.). In some examples, facilities 302 and 304 may be distributed between multiple devices and/or multiple locations as may serve a particular implementation.

Storage facility 302 may maintain (e.g., store) executable data used by processing facility 304 to perform any of the operations described herein. For example, storage facility 302 may store instructions 306 that may be executed by processing facility 304 to perform any of the operations described herein. Instructions 306 may be implemented by any suitable application, software, code, and/or other executable data instance. Storage facility 302 may also maintain any data received, generated, managed, used, and/or transmitted by processing facility 304.

Processing facility 304 may be configured to perform (e.g., execute instructions 306 stored in storage facility 302 to perform) various operations. For example, processing facility 304 may direct an acoustic stimulation generator to apply acoustic stimulation to a recipient of a cochlear implant during an insertion procedure in which an electrode lead coupled to the cochlear implant is supposed to be inserted into a cochlea of the recipient, direct the cochlear implant to use an electrode on the electrode lead to record an evoked response signal that occurs within the recipient in response to the acoustic stimulation, detect an anomaly in the evoked response signal, and determine, based on the anomaly, that the electrode lead is being inserted into a vestibular canal instead of into the cochlea. These and other operations that may be performed by processing facility 304 are described in more detail herein.

Figure 4:
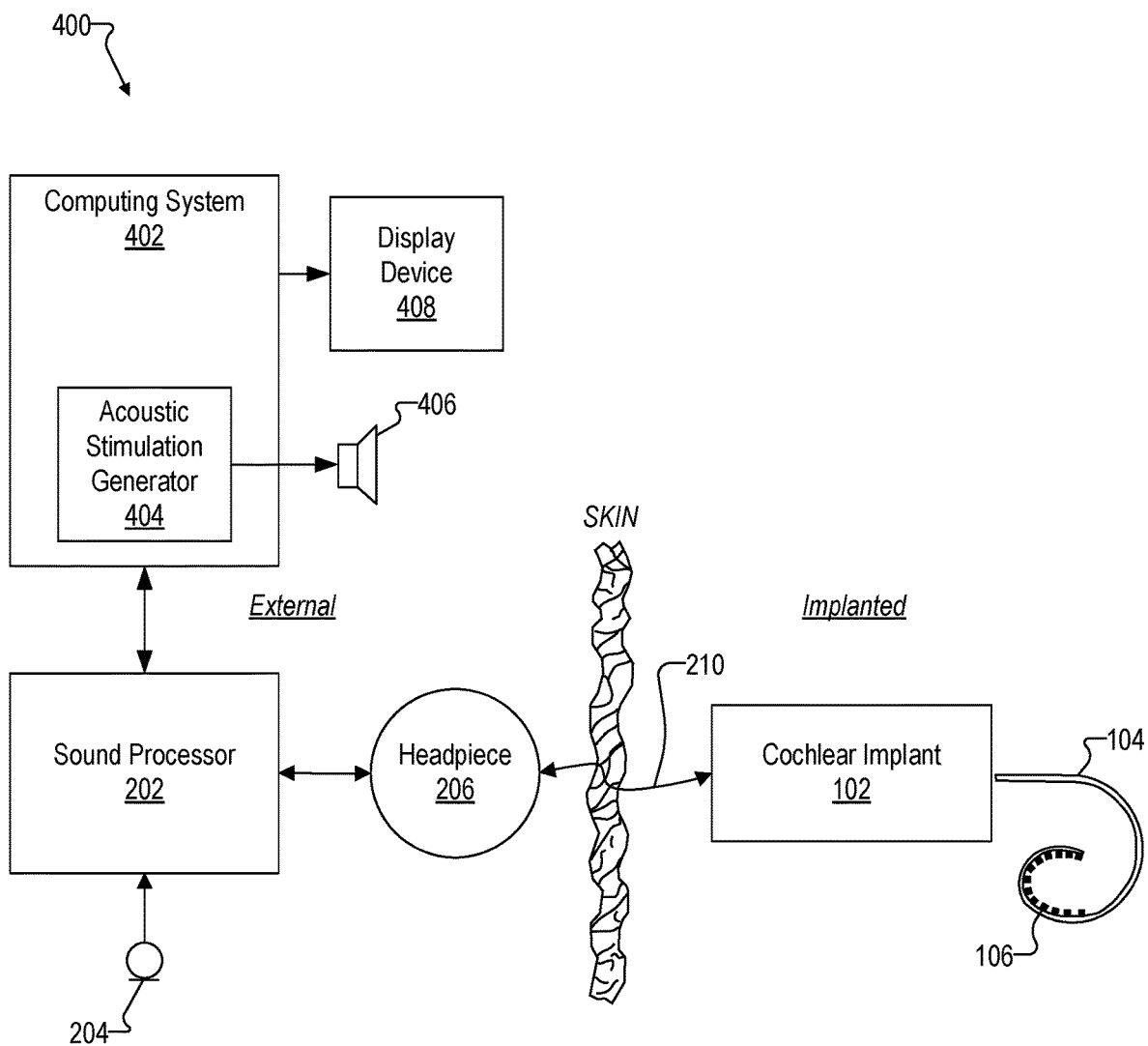
FIGS. 4-5 shows an exemplary implementations of the diagnostic system of FIG. 3.

Diagnostic system 300 may be implemented in any suitable manner. For example, FIG. 4 shows an exemplary configuration 400 in which diagnostic system 300 is implemented by a computing system 402 configured to communicatively couple to sound processor 202. As shown, computing system 402 may include an acoustic stimulation generator 404 communicatively coupled to a speaker 406. Computing system 402 is also communicatively coupled to a display device 408. While computing system 402 is described herein as being be coupled to sound processor 202, computing system 402 may be alternatively coupled to any other implementation of processing unit 108 as may serve a particular implementation.

Computing system 402 may be implemented by any suitable combination of hardware (e.g., one or more computing devices) and software. For example, computing system 402 may be implemented by a computing device programmed to perform one or more fitting operations with respect to a recipient of a cochlear implant. To illustrate, computing system 402 may be implemented by a desktop computer, a mobile device (e.g., a laptop, a smartphone, a tablet computer, etc.), and/or any other suitable computing device as may serve a particular implementation. As an example, computing system 402 may be implemented by a mobile device configured to execute an application (e.g., a "mobile app") that may be used by a user (e.g., the recipient, a clinician, and/or any other user) to control one or more settings of sound processor 202 and/or cochlear implant 102 and/or perform one or more operations (e.g., diagnostic operations) with respect to data generated by sound processor 202 and/or cochlear implant 102.

Acoustic stimulation generator 404 may be implemented by any suitable combination of components configured to generate acoustic stimulation. In some examples, the acoustic stimulation may include one or more tones having one or more stimulus frequencies. Additionally or alternatively, the acoustic stimulation may include any other type of acoustic content that has at least a particular stimulus frequency of interest. Speaker 406 may be configured to deliver the acoustic stimulation generated by acoustic stimulation generator 404 to the recipient. For example, speaker 406 may be implemented by an ear mold configured to be placed in or near an entrance to an ear canal of the recipient.

Display device 408 may be implemented by any suitable device configured to display graphical content generated by computing system 402. For example, display device 408 may display one or more graphs of evoked responses recorded by an electrode disposed on electrode lead 104. Display device 408 is shown in FIG. 4 as an external device configured to display content generated by computing system 402. Additionally or alternatively, computing system 402 may include display device 408 as an integrated display in certain implementations.

Figure 5:
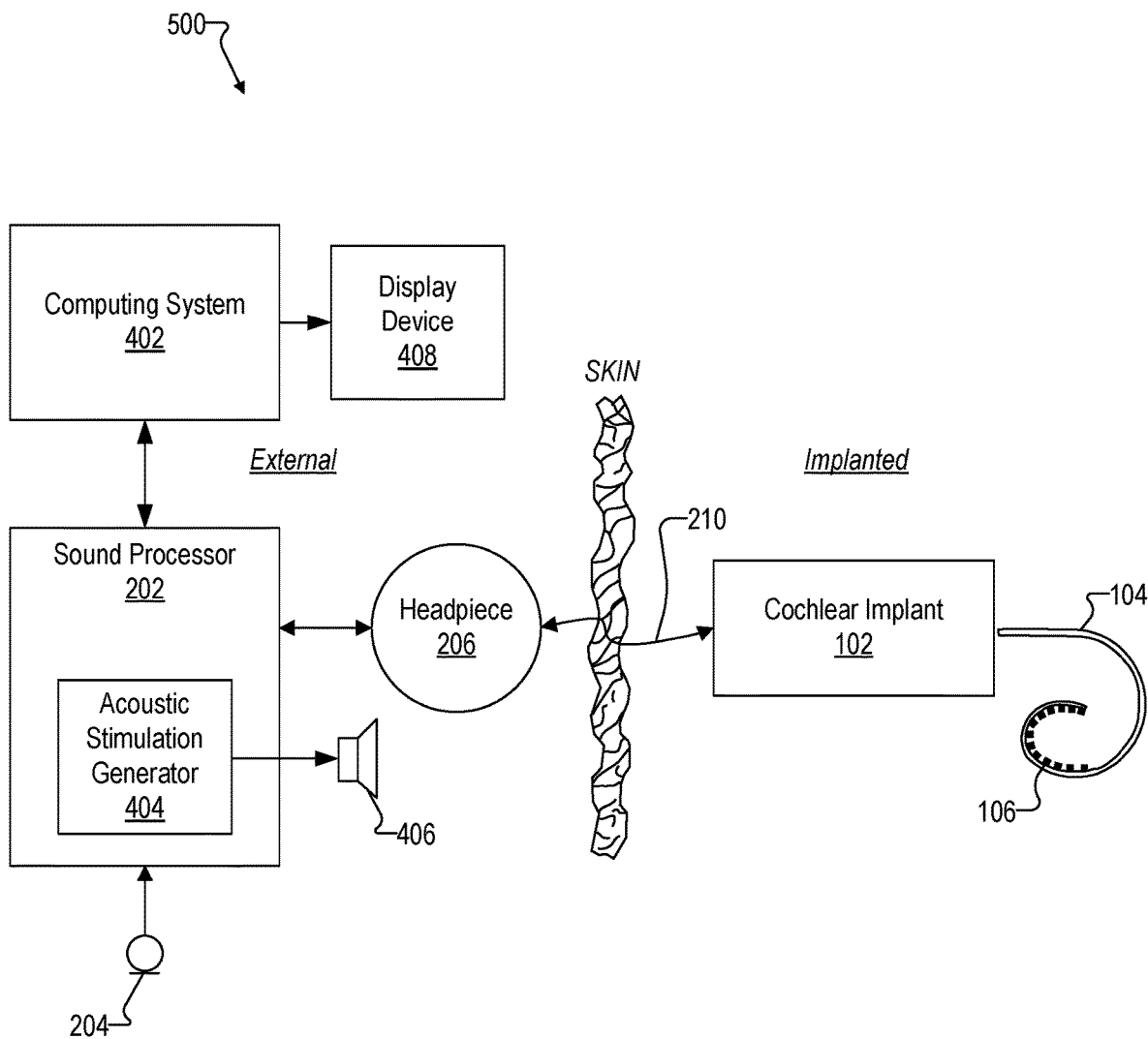

FIG. 5 shows another exemplary configuration 500 in which diagnostic system 400 is implemented by computing system 402. In configuration 500, acoustic stimulation generator 404 is included in sound processor 202. For example, sound processor 202 may be implemented by a bimodal sound processor (i.e., a sound processor configured to direct cochlear implant 102 to apply electrical stimulation to a recipient and acoustic stimulation generator 404 to apply acoustic stimulation to the recipient). In some examples, speaker 406 may be implemented by an audio ear hook that connects to sound processor 202.

Various operations that may be performed by diagnostic system 300 (e.g., processing facility 304) will now be described. It will be recognized that diagnostic system 300 may perform additional or alternative operations to those described herein as may serve a particular implementation.

In some examples, diagnostic system 300 may monitor an evoked response signal that occurs during a lead insertion procedure. To this end, diagnostic system 300 may direct an acoustic stimulation generator (e.g., acoustic stimulation generator 404) to apply acoustic stimulation to a recipient of a cochlear implant (e.g., cochlear implant 102) during an insertion procedure in which an electrode lead (e.g., electrode lead 104) coupled to the cochlear implant is supposed to be inserted into a cochlea of the recipient. The acoustic stimulation may include a single tone (e.g., a single frequency), multiple tones (e.g., multiple frequencies), and/or any other type of acoustic signal. The acoustic generator may apply the acoustic stimulation to the recipient in any suitable manner (e.g., by way of loudspeaker 406).

Diagnostic system 300 may be further configured to direct the cochlear implant to use an electrode on the electrode lead to record an evoked response signal that occurs within the recipient in response to the acoustic stimulation. Any electrode may be used as the recording electrode (i.e., the electrode used to record the evoked response signal). For example, the most apical electrode (i.e., the electrode most distally located on the electrode lead) may be used as the recording electrode.

While monitoring the evoked response signal, diagnostic system 300 may detect an anomaly in the evoked response signal and, based on the anomaly, determine that the electrode lead is being inserted into a vestibular canal instead of into the cochlea.

To illustrate, the acoustic stimulation applied by the acoustic stimulation generator may have a relatively low frequency (e.g., 500 Hz). This relatively low frequency corresponds to a location that is relatively deep within the cochlea (e.g., close to the apex of the cochlea). As such, as the practitioner advances the electrode lead further into the cochlea, an amplitude of the evoked response signal recorded by the electrode (e.g., the most apical electrode) on the electrode lead will increase as long as the electrode lead is being properly advanced within the cochlea. If the evoked response amplitude recorded by the electrode differs in one or more ways from what is expected (an anomaly), diagnostic system 300 may determine that the electrode lead has been misplaced in a vestibular canal.

Figure 6A:
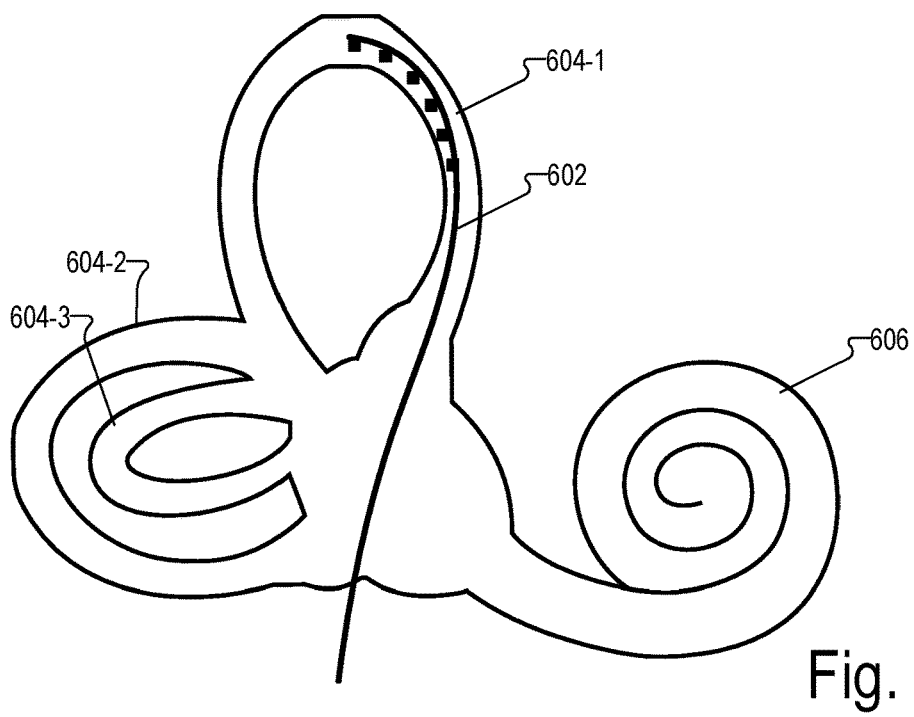
FIG. 6A illustrates an exemplary procedure in which an electrode lead 602 is inadvertently inserted into a vestibular canal instead of into the cochlea.

FIG. 6A illustrates an exemplary procedure in which an electrode lead 602 is inadvertently inserted into a vestibular canal 604-1 instead of into the cochlea 606. It will be recognized that electrode lead 602 may alternatively be inadvertently inserted into one of the other vestibular canals 604-2 or 604-3.

Figure 6B:
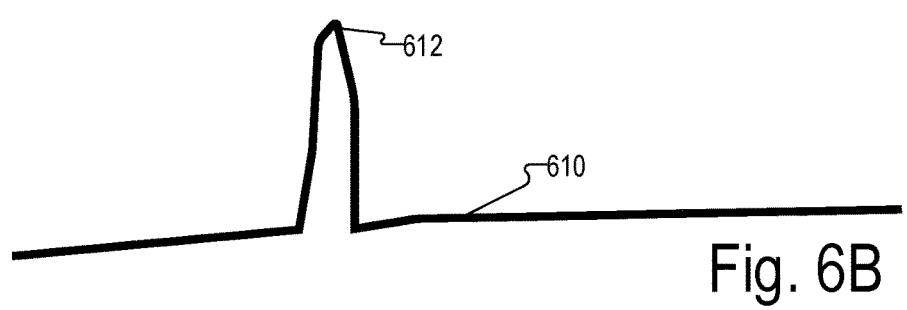
FIGS. 6B-6C show an exemplary evoked response signal that may be generated in response to acoustic stimulation during the procedure shown in FIG. 6A.

FIG. 6B shows an exemplary evoked response signal 610 that may be generated in response to acoustic stimulation during the procedure shown in FIG. 6A. As shown by peak 612, the amplitude of the evoked response signal 610 may increase as the recording electrode gets close to the entrance to the cochlea 606 and then decrease quickly as the electrode goes into vestibular canal 602 and gets further away from cochlea 606. Hence, in some examples, diagnostic system 300 may detect an occurrence of peak 612 (i.e., an amplitude change above a predetermined threshold), an increase in slope of evoked response signal 610 above a predetermined threshold within a certain amount of time, and/or decrease in slope of evoked response signal 610 below a predetermined threshold within a certain amount of time. In response to detecting one or more of these characteristics of evoked response signal 610, diagnostic system 300 may determine that electrode lead is not within cochlea 606 and instead within vestibular canal 604-1.

Figure 6C:
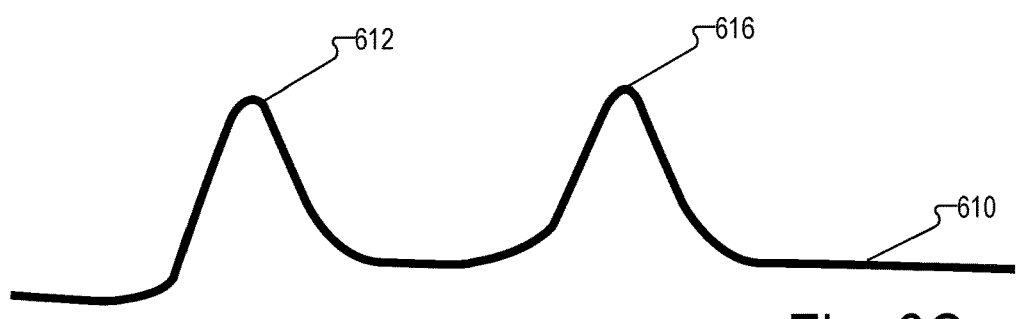

Due to the circular nature of the vestibular canal 604-1, if the practitioner continues to insert the electrode lead 602 into the vestibular canal 604-1, the recording electrode may start to get closer to the cochlea 606 again as the recording electrode goes around the circular shape of the vestibular canal. Hence, the amplitude of evoked response signal 610 may again increase, as shown by peak 614 in FIG. 6C. Detection of multiple peaks 612 and 614 (or multiple increases or decreases in slope) may serve as further confirmation that electrode lead 602 is in the vestibular canal 604-1.

Figure 6D:
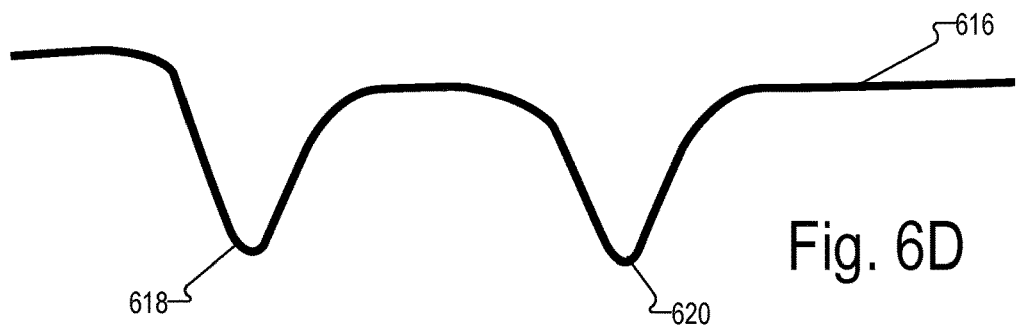
FIG. 6D shows a phase of an evoked response signal.

FIG. 6D shows a phase (i.e., delay) 616 of evoked response signal 610 as recorded by the recording electrode. The phase graph shown in FIG. 6D represents a delay in recording evoked response signal 610 compared to a time at which the acoustic stimulation is applied. The closer the recording electrode is to the cochlea, the lower the amplitude should be of the phase graph. For example, as shown by local minimums 618 and 620, the delay is at a minimum when the amplitude of evoked response signal 610 is at a maximum. In some examples, 300 may detect one or more changes in phase of evoked response signal 610 above a predetermined threshold, alone or in combination with changes in amplitude of evoked response signal 610, to determine that electrode lead 602 is in the vestibular canal 604-1.

Figure 7:
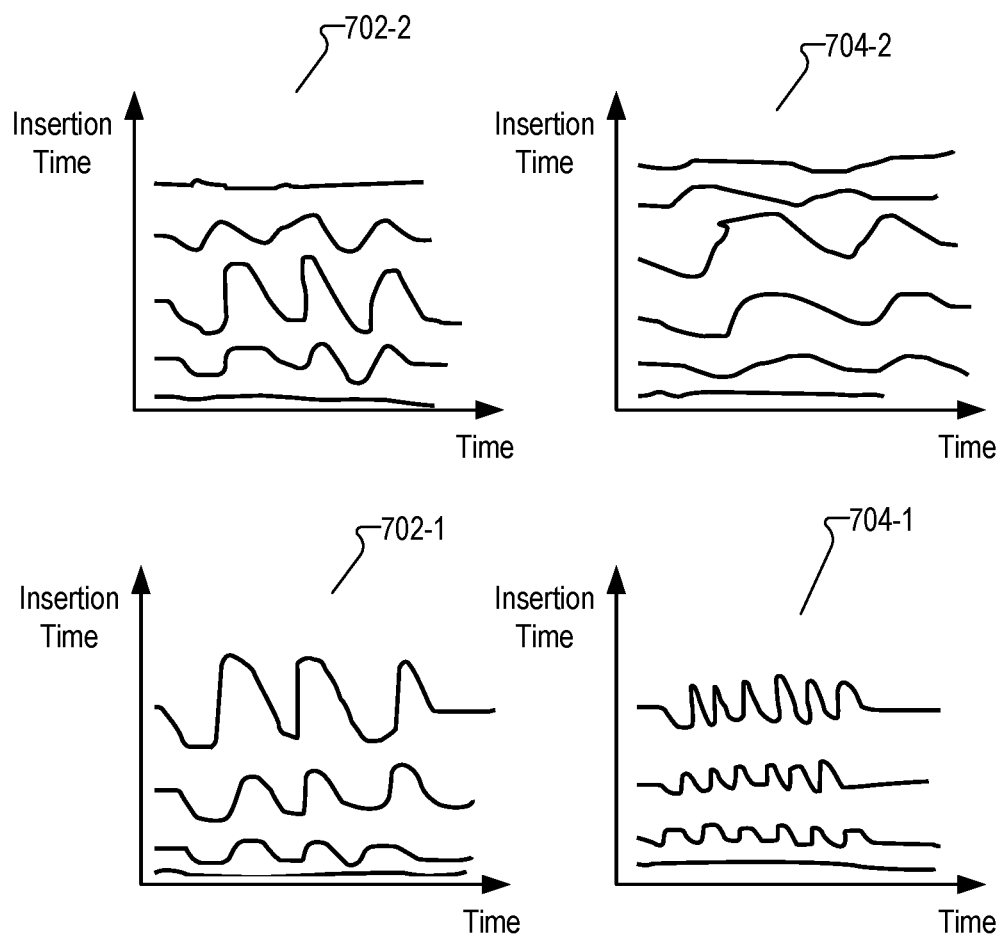
FIG. 7 shows various graphs.

Additionally or alternatively, diagnostic system 300 may determine that electrode lead 602 is in the vestibular canal 604-1 by comparing a frequency of a CM response and a frequency of an ANN response to the same acoustic stimuli. To illustrate, FIG. 7 shows a graph 702-1 of a CM response and a graph 704-1 of an ANN response during a normal insertion procedure in which an electrode lead is inserted into the cochlea. FIG. 7 also shows a graph 702-2 of a CM response and a graph 704-2 of an ANN response during an insertion procedure in which the electrode lead is inadvertently inserted into the vestibular canal. Each of the graphs shown in FIG. 7 are in the time domain.

As shown by graphs 702-1 and 704-1, a frequency of the ANN responses is greater than a frequency of the CM responses when the electrode lead is properly inserted into the cochlea. For example, a frequency of the ANN responses may be double that of the CM responses. This is due to the ANN responses being from neural structures that act as a rectifier to create double the frequency when alternative polarities are added. In contrast, CM responses, which are responses from the hair cells, follow the stimulus frequency.

However, as shown by graphs 702-2 and 704-2, a frequency of the ANN responses is less than a frequency of the CM responses when the electrode lead is inadvertently placed in the vestibular canal. This is due in part to mixing of cochlear fluid with vestibular fluid. Accordingly, diagnostic system 300 may determine that electrode lead 602 is in the vestibular canal 604-1 by detecting that the ANN response has a lower frequency than the CM response by more than a threshold amount.

Diagnostic system 300 may perform one or more remedial actions in response to determining that an electrode lead has been inadvertently inserted into a vestibular canal. For example, diagnostic system 300 may provide a notification (e.g., a message, a visible notification, an audible notification, etc.) to a practitioner performing the insertion procedure.

As another example, diagnostic system 300 may stop the insertion procedure in response to determining that the electrode lead has been inadvertently inserted into a vestibular canal. This may be performed in any suitable manner. For example, diagnostic system 300 may provide a notification for the practitioner to stop the insertion procedure. As another example, in cases where a computing system (e.g., a robotic surgical system) is being used to perform the insertion procedure, diagnostic system 300 may provide a command to the computing system to stop the insertion procedure.

As another example, diagnostic system 300 may cause the electrode lead to be retracted from the vestibular canal. This may be performed in any suitable manner. For example, diagnostic system 300 may provide a notification for the practitioner to retract the electrode lead. As another example, in cases where a computing system (e.g., a robotic surgical system) is being used to perform the insertion procedure, diagnostic system 300 may provide a command to the computing system that causes the computing system to retract the electrode lead.

In some examples, diagnostic system 300 may display any of the graphs described herein on a display device viewable by the practitioner and/or other personnel assisting in the insertion procedure. For example, diagnostic system 300 may direct a display device to display a graph of any of the evoked response signals described herein in substantially real-time during the insertion procedure.

Figure 8:
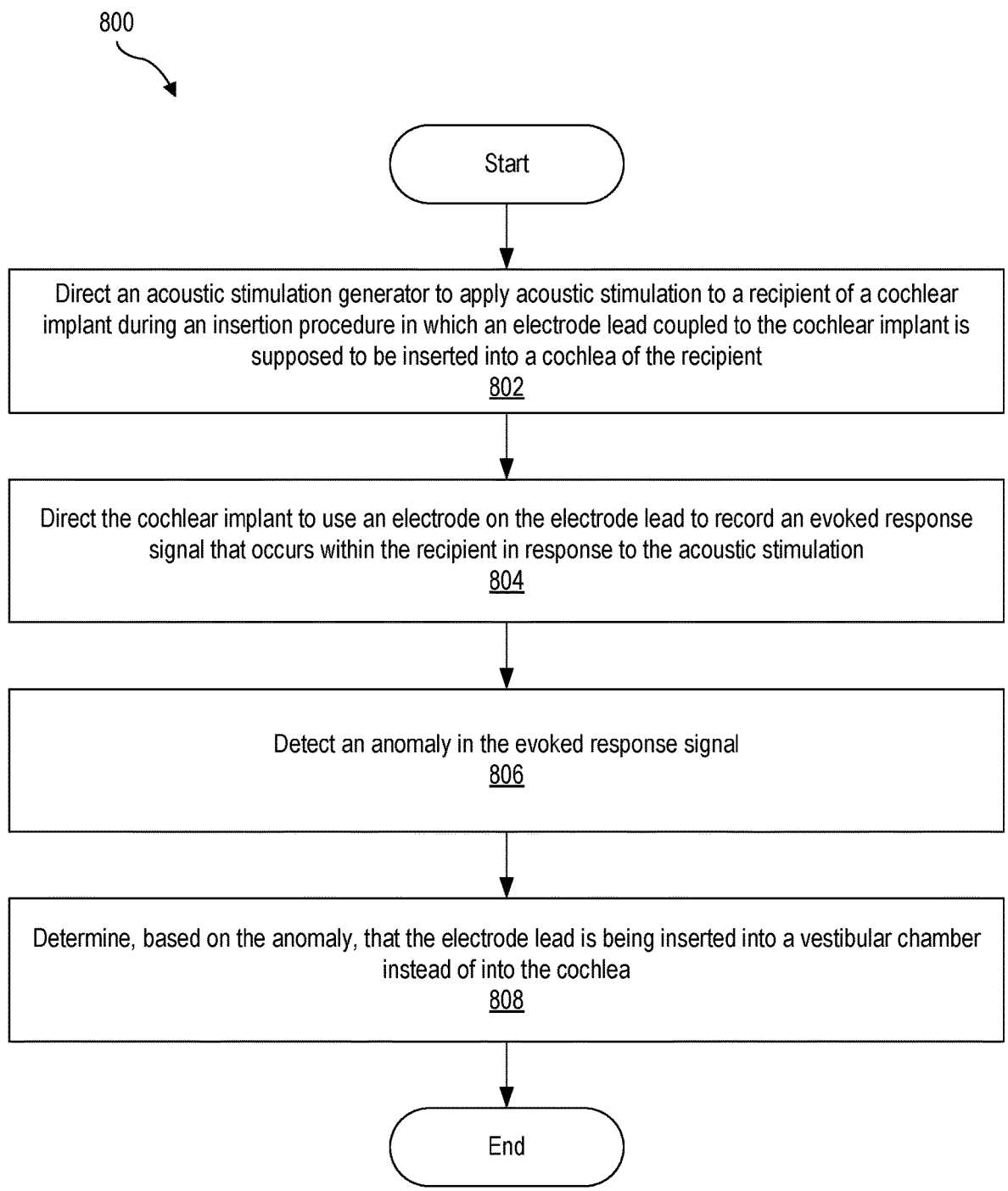
FIG. 8 illustrates an exemplary method.

FIG. 8 illustrates an exemplary method 800 that may be performed diagnostic system 300 or any implementation thereof. While FIG. 8 illustrates exemplary operations according to one embodiment, other embodiments may omit, add to, reorder, and/or modify any of the operations shown in FIG. 8.

At operation 802, a diagnostic system directs an acoustic stimulation generator to apply acoustic stimulation to a recipient of a cochlear implant during an insertion procedure in which an electrode lead coupled to the cochlear implant is supposed to be inserted into a cochlea of the recipient. Operation 802 may be performed in any of the ways described herein.

At operation 804, the diagnostic system directs the cochlear implant to use an electrode on the electrode lead to record an evoked response signal that occurs within the recipient in response to the acoustic stimulation. Operation 806 may be performed in any of the ways described herein. For example, the distal-most electrode or any other suitable electrode may be used as the recording electrode.

At operation 806, the diagnostic system detects an anomaly in the evoked response signal. Operation 806 may be performed in any of the ways described herein.

For example, the diagnostic system may detect the anomaly in the evoked response signal by detecting one or more local maximums of an amplitude of the evoked response signal that each occur within a threshold insertion time associated with the insertion procedure. The threshold insertion time may be representative of an insertion depth (e.g., the greater the insertion time, the greater the insertion depth and vice versa).

As another example, the diagnostic system may detect the anomaly in the evoked response signal by detecting a threshold change in amplitude of the evoked response signal that occurs within a threshold insertion time associated with the insertion procedure. another example, the diagnostic system may detect the anomaly in the evoked response signal by detecting a threshold change in a slope of the evoked response signal that occurs within a threshold insertion time associated with the insertion procedure.

As another example, the diagnostic system may detect the anomaly in the evoked response signal by detecting a local minimum of a phase of the evoked response signal that occurs within an threshold insertion time associated with the insertion procedure, the phase representing a delay in the electrode recording the evoked response signal compared to a time at which the acoustic stimulation is applied by the acoustic generator. In some examples, the detection of the local minimum of the phase may be detected concurrently with any of the other amplitude attributes (e.g., a local maximum, a slope, or a change) such that both phase and amplitude are taken into account when detecting the anomaly.

As another example, the diagnostic system may detect the anomaly in the evoked response signal by detecting that a frequency of the ANN response is lower than a frequency of the CM response by more than a threshold amount.

At operation 808, the diagnostic system determines, based on the anomaly, that the electrode lead is being inserted into a vestibular canal instead of into the cochlea. Operation 808 may be performed in any of the ways described herein.

In some examples, a non-transitory computer-readable medium storing computer-readable instructions may be provided in accordance with the principles described herein.

The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 9:
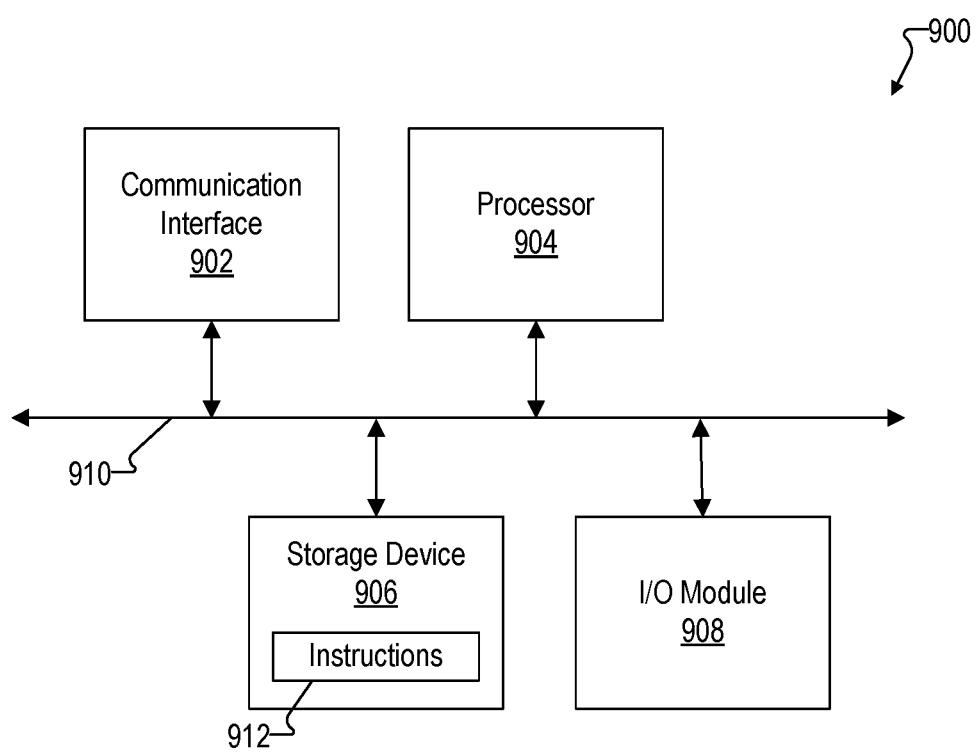
FIG. 9 illustrates an exemplary computing device.

FIG. 9 illustrates an exemplary computing device 900 that may be specifically configured to perform one or more of the processes described herein. To that end, any of the systems, processing units, and/or devices described herein may be implemented by computing device 900.

As shown in FIG. 9, computing device 900 may include a communication interface 902, a processor 904, a storage device 906, and an input/output ("I/O") module 908 communicatively connected one to another via a communication infrastructure 910. While an exemplary computing device 900 is shown in FIG. 9, the components illustrated in FIG. 9 are not intended to be limiting. Additional or alternative components may be used in other embodiments. Components of computing device 900 shown in FIG. 9 will now be described in additional detail.

Communication interface 902 may be configured to communicate with one or more computing devices. Examples of communication interface 902 include, without limitation, a wired network interface (such as a network interface card), a wireless network interface (such as a wireless network interface card), a modem, an audio/video connection, and any other suitable interface.

Processor 904 generally represents any type or form of processing unit capable of processing data and/or interpreting, executing, and/or directing execution of one or more of the instructions, processes, and/or operations described herein. Processor 904 may perform operations by executing computer-executable instructions 912 (e.g., an application, software, code, and/or other executable data instance) stored in storage device 906.

Storage device 906 may include one or more data storage media, devices, or configurations and may employ any type, form, and combination of data storage media and/or device. For example, storage device 906 may include, but is not limited to, any combination of the non-volatile media and/or volatile media described herein. Electronic data, including data described herein, may be temporarily and/or permanently stored in storage device 906. For example, data representative of computer-executable instructions 912 configured to direct processor 904 to perform any of the operations described herein may be stored within storage device 906. In some examples, data may be arranged in one or more databases residing within storage device 906.

I/O module 908 may include one or more I/O modules configured to receive user input and provide user output. I/O module 908 may include any hardware, firmware, software, or combination thereof supportive of input and output capabilities. For example, I/O module 908 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 908 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 908 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions;
a processor communicatively coupled to the memory and configured to execute the instructions to:
  direct an acoustic stimulation generator to apply acoustic stimulation to a recipient of a cochlear implant during an insertion procedure in which an electrode lead coupled to the cochlear implant is configured to be inserted into a cochlea of the recipient;
  direct the cochlear implant to use an electrode on the electrode lead to record an evoked response signal that occurs within the recipient in response to the acoustic stimulation;
  detect an anomaly in the evoked response signal, the detecting the anomaly comprising detecting a plurality of local maximums of an amplitude of the evoked response signal that each occur within a threshold insertion time associated with the insertion procedure, the plurality of local maximums indicative of the electrode lead being inserted into a vestibular canal instead of into the cochlea; and
  determine, based on the detection of the plurality of local maximums of the amplitude of the evoked response signal, that the electrode lead is being inserted into the vestibular canal instead of into the cochlea.

2. The system of claim 1, further comprising detecting an additional anomaly in the evoked response signal, wherein the detecting that the electrode lead is being inserted into the vestibular canal is further based on the detecting the additional anomaly.

3. The system of claim 2, wherein the detecting of the additional anomaly in the evoked response signal comprises detecting a local minimum of a phase of the evoked response signal that occurs within the threshold insertion time, the phase representing a delay in the electrode recording the evoked response signal compared to a time at which the acoustic stimulation is applied by the acoustic generator.

4. The system of claim 2, wherein the detecting of the additional anomaly in the evoked response signal comprises detecting a threshold change in the amplitude of the evoked response signal that occurs within a threshold insertion time associated with the insertion procedure.

5. The system of claim 2, wherein the detecting of the additional anomaly in the evoked response signal comprises detecting a threshold change in a slope of the evoked response signal that occurs within a threshold insertion time associated with the insertion procedure.

6. The system of claim 2, wherein the detecting of the additional anomaly in the evoked response signal comprises detecting a local minimum of a phase of the evoked response signal that occurs within a threshold time associated with the insertion procedure, the phase representing a delay in the electrode recording the evoked response signal compared to a time at which the acoustic stimulation is applied by the acoustic generator.

7. The system of claim 2, wherein the evoked response signal comprises an auditory nerve neurophonics (ANN) response and a cochlear microphonic (CM) response, and wherein the detecting of the additional anomaly in the evoked response signal comprises detecting that a frequency of the ANN response is lower than a frequency of the CM response by more than a threshold amount.

8. The system of claim 1, wherein the processor is further configured to execute the instructions to perform a remedial action in response to the determining that the electrode lead is being inserted into the vestibular canal.

9. The system of claim 8, wherein the performing of the remedial action comprises one or more of providing a notification, stopping the insertion procedure, or causing the electrode lead to be retracted from the vestibular canal.

10. The system of claim 9, wherein the stopping of the insertion procedure comprises providing an instruction to a device being used to perform the insertion procedure, the instruction configured to direct the device to stop the insertion procedure.

11. The system of claim 9, wherein the processor is further configured to execute the instructions to direct a display device to display a graph of the evoked response signal in substantially real-time during the insertion procedure.

12. The system of claim 1, wherein the evoked response signal is an electrocochleographic (ECochG) signal.

13. A method comprising:
directing, by a diagnostic system, an acoustic stimulation generator to apply acoustic stimulation to a recipient of a cochlear implant during an insertion procedure in which an electrode lead coupled to the cochlear implant is configured to be inserted into a cochlea of the recipient;
directing, by the diagnostic system, the cochlear implant to use an electrode on the electrode lead to record an evoked response signal that occurs within the recipient in response to the acoustic stimulation;
detecting, by the diagnostic system, an anomaly in the evoked response signal, the detecting the anomaly comprising detecting a plurality of local maximums of an amplitude of the evoked response signal that each occur within a threshold insertion time associated with the insertion procedure, the plurality of local maximums indicative of the electrode lead being inserted into a vestibular canal instead of into the cochlea; and
determining, by the diagnostic system based on the detection of the plurality of local maximums of the amplitude of the evoked response signal, that the electrode lead is being inserted into the vestibular canal instead of into the cochlea.

14. The method of claim 13, further comprising detecting an additional anomaly in the evoked response signal, wherein the detecting that the electrode lead is being inserted into the vestibular canal is further based on the detecting the additional anomaly.

15. The method of claim 14, wherein the detecting of the additional anomaly in the evoked response signal further comprises detecting a local minimum of a phase of the evoked response signal that occurs within the threshold insertion time, the phase representing a delay in the electrode recording the evoked response signal compared to a time at which the acoustic stimulation is applied by the acoustic generator.

16. The method of claim 14, wherein the detecting of the additional anomaly in the evoked response signal comprises detecting a threshold change in amplitude of the evoked response signal that occurs within a threshold insertion time associated with the insertion procedure.

17. The method of claim 14, wherein the detecting of the additional anomaly in the evoked response signal comprises detecting a local minimum of a phase of the evoked response signal that occurs within a threshold time associated with the insertion procedure, the phase representing a delay in the electrode recording the evoked response signal compared to a time at which the acoustic stimulation is applied by the acoustic generator.

18. The method of claim 14, wherein the evoked response signal comprises an auditory nerve neurophonics (ANN) response and a cochlear microphonic (CM) response, and wherein the detecting of the additional anomaly in the evoked response signal comprises detecting that a frequency of the ANN response is lower than a frequency of the CM response by more than a threshold amount.

19. A non-transitory computer-readable medium storing instructions that, when executed, direct a processor of a computing device to:
direct an acoustic stimulation generator to apply acoustic stimulation to a recipient of a cochlear implant during an insertion procedure in which an electrode lead coupled to the cochlear implant is configured to be inserted into a cochlea of the recipient;
direct the cochlear implant to use an electrode on the electrode lead to record an evoked response signal that occurs within the recipient in response to the acoustic stimulation;
detect an anomaly in the evoked response signal, the detecting the anomaly comprising detecting a plurality of local maximums of an amplitude of the evoked response signal that each occur within a threshold insertion time associated with the insertion procedure, the plurality of local maximums indicative of the electrode lead being inserted into a vestibular canal instead of into the cochlea; and
determine, based on the detection of the plurality of local maximums of the amplitude of the evoked response signal, that the electrode lead is being inserted into the vestibular canal instead of into the cochlea.

* * * * *